(12) United States Patent
Friedman et al.

(10) Patent No.: US 9,307,921 B2
(45) Date of Patent: *Apr. 12, 2016

(54) NON-INVASIVE MONITORING OF PHYSIOLOGICAL CONDITIONS

(71) Applicant: Mayo Foundation for Medical Education and Research, Rochester, MN (US)

(72) Inventors: Paul A. Friedman, Rochester, MN (US); Kevin E. Bennet, Rochester, MN (US); Charles J. Bruce, Rochester, MN (US); Virend K. Somers, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/577,924

(22) Filed: Dec. 19, 2014

(65) Prior Publication Data

US 2015/0105640 A1    Apr. 16, 2015

Related U.S. Application Data

(63) Continuation of application No. 13/810,064, filed as application No. PCT/US2011/043883 on Jul. 13, 2011, now Pat. No. 8,948,854.

(60) Provisional application No. 61/364,317, filed on Jul. 14, 2010.

(51) Int. Cl.
*A61B 5/04*   (2006.01)
*A61B 5/0452*   (2006.01)
*A61B 5/0472*   (2006.01)
*A61B 5/145*   (2006.01)
*A61B 5/00*   (2006.01)
*A61B 5/1477*   (2006.01)

(52) U.S. Cl.
CPC ......... *A61B 5/04012* (2013.01); *A61B 5/0006* (2013.01); *A61B 5/0472* (2013.01); *A61B 5/04525* (2013.01); *A61B 5/1477* (2013.01); *A61B 5/14532* (2013.01); *A61B 5/14546* (2013.01)

(58) Field of Classification Search
CPC ............ A61B 5/0006; A61B 5/04012; A61B 5/04525; A61B 5/0472; A61B 5/14532; A61B 5/14546; A61B 5/1477
See application file for complete search history.

(56) References Cited

U.S. PATENT DOCUMENTS

| | | | |
|---|---|---|---|
| 5,560,368 A | 10/1996 | Berger | |
| 6,480,734 B1 | 11/2002 | Zhang | |
| 7,218,960 B1 | 5/2007 | Min | |
| 7,704,227 B2 * | 4/2010 | Moberg et al. | 604/65 |
| 8,948,854 B2 | 2/2015 | Friedman | |
| 2005/0075673 A1 | 4/2005 | Warkentin | |

(Continued)

OTHER PUBLICATIONS

Aslam et al., "Electrocardiography is unreliable in detecting potentially lethal hyperkalaemia in haemodialysis patients," *Nephrol. Dial. Transplant.*, 17(9):1639-1642, Sep. 2002.

(Continued)

*Primary Examiner* — George Manuel
(74) *Attorney, Agent, or Firm* — Fish & Richardson P.C.

(57) ABSTRACT

This document provides methods and materials related to the non-invasive measurement of analytes in blood.

27 Claims, 3 Drawing Sheets

(56) References Cited

U.S. PATENT DOCUMENTS

| | | |
|---|---|---|
| 2006/0155200 A1 | 7/2006 | Ng |
| 2008/0033260 A1 | 2/2008 | Sheppard et al. |
| 2008/0033313 A1 | 2/2008 | Couderc |
| 2008/0208069 A1 | 8/2008 | John et al. |
| 2009/0311796 A1* | 12/2009 | Griss et al. ............... 436/166 |
| 2010/0004517 A1 | 1/2010 | Bryenton et al. |
| 2013/0184599 A1 | 7/2013 | Friedman |

OTHER PUBLICATIONS

Bellardine-Black et al., "Is surface ECG a useful surrogate for subcutaneous ECG?" *Pacing Clin Electrophysiol.*, 33(2):135-145, Epub Nov. 18, 2009.

Berbari et al., "Noninvasive technique for detection of electrical activity during the P-R segment," *Circulation*, 48(5):1005-1013, Nov. 1973.

Bleyer et al., "Characteristics of sudden death in hemodialysis patients," *Kidney International*, 2006;69:2268-2273.

Bleyer et al., "Sudden and cardiac death rates in hemodialysis patients," *Kidney International*, 1999;55:1553-1559.

Blumberg et al., "Effect of various therapeutic approaches on plasma potassium and major regulating factors in terminal renal failure." *The American Journal of Medicine*, 1988;85:507-512.

Burnham and Anderson, "Information and Likelihood Theory: A Basis for Model Selection and Inference Model Selection and Multimodel Inference: A Practical Information-Theoretic Approach," New York: Springer, 2002:49-96.

Cain and Harken, "On Surgical treatment of diastolic dysfunction," *J Card Surg*, 12(4):238-239, Jul.-Aug. 1997.

Chapagain and Ashman, "Hyperkalaemia in the age of aldosterone antagonism," *QJM : Monthly Journal of the Association of Physicians*, 2012;105:1049-1057.

Chernenko, "ECG processing—R-peaks detection," Librow [online] Retrieved from the Internet: <URL: http://web.archive.org/web/20121115151614/http://www.librow.com/cases/case-2> captured Nov. 15, 2012, 3 pages.

Corsi et al., "ECG-based blood potassium estimates," presented at the Second Conference on Cardiac Arrest & Sudden Death—Cardiovascular Therapy, Copenhagen, Denmark, Jun. 16-18, 2011, 8 pages.

Desai, "Hyperkalemia associated with inhibitors of the renin-angiotensin-aldosterone system: balancing risk and benefit," *Circulation.*, 118(16):1609-1611, Oct. 14, 2008.

Dittrich and Walls, "Hyperkalemia: ECG manifestations and clinical considerations," *Journal of Emergency Medicine*, 1986;4:449-455.

Einhorn, "The frequency of hyperkalemia and its significance in chronic of kidney disease," *Archives Internal Medicine*, 2009;169:1156-1162.

Frohnert et al., "Statistical investigation of correlations between serum potassium levels and electrocardiographic findings in patients on intermittent hemodialysis therapy," *Circulation*, 41(4):667-676, Apr. 1970.

Goyal et al., "Serum potassium levels and mortality in acute myocardial infarction," *JAMA*, 2012;307:157-164.

Helfenbein et al., "An algorithm for QT interval monitoring in neonatal intensive care units," *J Electrocardiol.*, 40(6 Suppl):S103-S110, Nov.-Dec. 2007.

Herzog et al., "Sudden cardiac death and dialysis patients" *Semin Dial.*, 21(4):300-307, Epub Jul. 8, 2008.

Jain et al., "Predictors of hyperkalemia and death in patients with cardiac and renal disease," *American Journal of Cardiology*, 2012;109:1510-1513.

Juurlink et al., "Rates of hyperkalemia after publication of the Randomized Aldactone Evaluation Study," *New England Journal of Medicine*, 2004;351:543-551.

Juurlink et al., "Rates of hyperkalemia after publication of the Randomized Aldactone Evaluation Study," *N Engl J Med.*, 351(6):543-551, Aug. 5, 2004.

Khanna and White, "The management of hyperkalemia in patients with cardiovascular disease," *Am. J Med.*, 122(3):215-221, Mar. 2009

Kovesdy et al., "Serum and dialysate potassium concentrations and survival in hemodialysis patients," *Clin J Am Soc Nephrol.*, 2(5):999-1007, Epub Aug. 16, 2007.

Laks and Elek, "The effect of potassium on the electrocardiogram: clinical and transmembrane correlations," *Dis Chest.*, 51(6):573-586, Jun. 1967.

Lanari et al., "Electrocardiographic effects of potassium. I. Perfusion through the coronary bed," *Am Heart J.*, 67:357-363, Mar. 1964.

Levine, "Electrolyte imbalance and the electrocardiogram," *Modern Concepts of Cardiovascular Disease*, 1954;23:246-249.

Malhis et al., "Changes in QT intervals in patients with end-stage renal disease before and after hemodialysis," *Saudi J Kidney Dis Trans.*, 21(3):460-465, May 2010.

McHenry Martin and Furnas, "Identifying drug-induced changes in electrocardiogram results of elderly individuals," *The Consultant Pharmacist*, 12 pages, Jan. 1997, [retrieved on Feb. 17, 2010], Retrieved from the Internet: <URL: http://www.ascp.com/publications/tcp/1997/jan/idicerei.html>.

Panikkath et al., "Prolonged Tpeak-to-tend interval on the resting ECG is associated with increased risk of sudden cardiac death," *Circ Arrhythm Electrophysiol.*, 4(4):441-447, Epub May 18, 2011.

Papadimitriou et al., "Electrocardiographic changes and plasma potassium levels in patients on regular haemodialysis," *Br Med J.*, 2(5704):268-269, May 2, 1970.

Perl and Chan, "Timing of sudden death relative to the hemodialysis procedure," *Nature Clinical Practice Nephrology*, 2006;2:668-669.

Seven et al., "Noninvasive potassium measurements from ECG analysis during hemodialysis sessions," *Computers in Cardiology*, 36:821-824, Sep. 2009.

Seven et al., "Noninvasive potassium measurements from ECG analysis during hemodialysis sessions," *Computers in Cardiology*, pp. 821,824, Sep. 13-16, 2009.

Seven et al., "Calcium and potassium changes during haemodialysis alter ventricular repolarization duration: in vivo and in silico analysis," *Nephrol Dial Transplant.*, 23(4):1378-1386, Epub Nov. 28, 2007.

Seven et al., "Electrocardiographic changes during hemodiafiltration with different potassium removal rates," *Blood Purif.*, 21(6):381-388, 2003.

Sterns et al., "Ion-exchange resins for the treatment of hyperkalemia: are they safe and effective?" *Journal of the American Society of Nephrology : JASN*, 2010;21:733-735.

Surawicz, "Electrolytes and the electrocardigraim," *Postgrad. Med.*, 55(6):123-129, Jun. 1974.

Surawicz, "Electrolytes and the electrocardiogram," *Am. J. Cardiol.*, 12(5):656-662, Nov. 1963.

Surawicz, "Relationship between electrocardiogram and electrolytes," *Am. Heart J.*, 73(6):814-834, Jun. 1967 .

University of Kentucky, "Clinical Lab Reference Range Guide," dated Mar. 14, 2006, Retrieved from the Internet: http://www.hosp.uky.edu/Clinlab/report.pdf, 102 pages.

VanderArk et al., "Electrolytes and the electrocardiogram," *Cardiovasc. Clin.*, 5(3):269-294, 1973.

Vogt et al., "Role of physical activity in recurrence of atrial fibrillation: results from a novel, prolonged-use and wearable ECG patch," *J Am Coll Cardiol.*, 2014;63:12_5.

Webster et al., "Recognising signs of danger: ECG changes resulting from an abnormal serum potassium concentration," *Emergency Medicine Journal*, 2002;19:74-77.

Weiner et al., "Disorders of Potassium Metabolism," Johnson and Feehally ed. *Comprehensive Clinical Nephrology*. Philadelphia, PA: Saunders Elsevier, 2010:118-129.

Wrenn et al., "The ability of physicians to predict hyperkalemia from the ECG," *Ann. Emerg. Med.*, 20(11):1229-1232, Nov. 1991.

Yan and Antzelevitch, "Cellular basis for the normal T wave and the electrocardiographic manifestations of the long-QT syndrome," *Circulation.*, 98(18):1928-1936, Nov. 3, 1998.

Zhang et al., "An algorithm for robust and efficient location of T-wave ends in electrocardiograms," *IEEE Trans Biomed Eng.*, 53(12 Pt 1):2544-2552, Dec. 2006.

International Preliminary Report on Patentability for PCT/US2011/043883, mailed Jan. 15, 2013, 5 pages.

International Search Report and Written Opinion for PCT/US2011/043883 mailed Feb. 10, 2012, 8 pages.

International Search Report and Written Opinion for PCT/US2014/057811 mailed Jan. 7, 2015, 16 pages.

\* cited by examiner

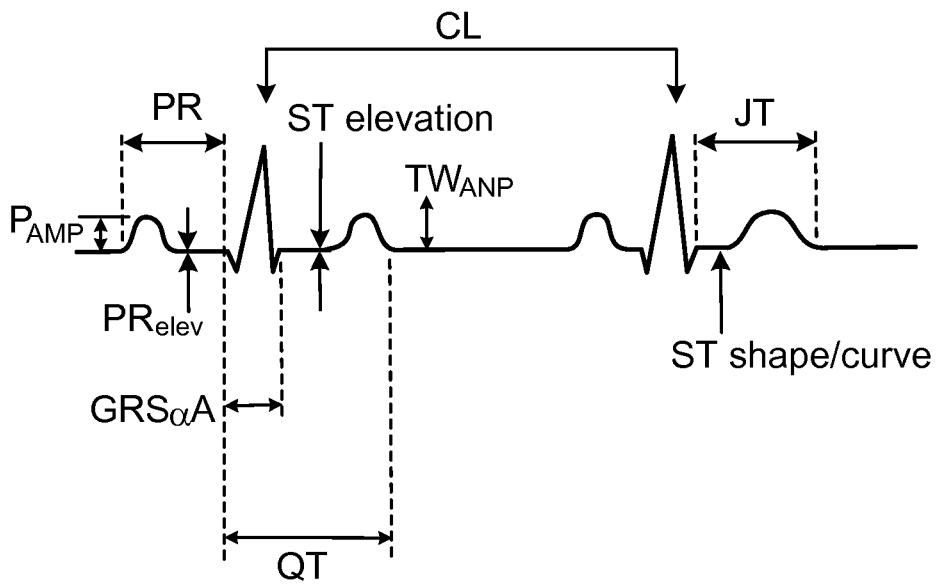

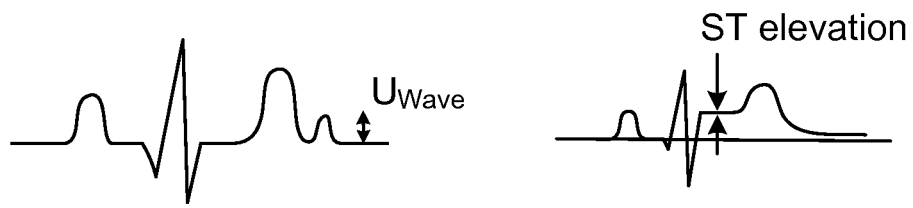

$\Delta_\varepsilon = F_{11} * PR_\Delta + F_{21} * P_{AM} + F_{31} * PR_{ELEV} + F_{41} * \alpha R_s d$ $\Delta_{\varepsilon n} = F_{1n} * PR_\Delta + F_{2n} * P_{AM}$ $\Delta_{\varepsilon i}$ = change in values for electrolyte (i)

$\varepsilon i$ = potassium
    $\varepsilon 2$ = calcium $F_1 = F_n$ = weight for specific ECG change
    for a given electrolyte
        e.g. $F_{11}$ = weight factor for $PR_\Delta S$ for potassium
            $F_{12}$ = weight factor for $PR_\Delta S$ for calcium
            etc.

FIG. 2

NON-INVASIVE MONITORING OF PHYSIOLOGICAL CONDITIONS

CROSS-REFERENCE TO RELATED APPLICATIONS

This application is a continuation of U.S. application Ser. No. 13/810,064, filed Mar. 29, 2013, which is a National Stage application under 35 U.S.C. §371 of International Application No. PCT/US2011/043883, having an International Filing Date of Jul. 13, 2011, which claims the benefit of priority to U.S. Provisional Application Ser. No. 61/364,317, filed on Jul. 14, 2010. The disclosures of the prior applications are considered part of (and are incorporated by reference in) the disclosure of this application.

TECHNICAL FIELD

This document relates to methods and materials involved in non-invasively measuring analyte levels in blood and non-invasively detecting abnormal physiological conditions.

BACKGROUND

Measurement of electrolytes (e.g., sodium, potassium, calcium, and magnesium) and analytes (e.g., glucose) and assessment of blood levels of medications can be important in clinical medicine. This importance spans a large panoply of disease states including arrhythmias, heart failure, renal failure, and medication titration or adjustment. Assessment of these values involves access to blood—either by phlebotomy or other skin puncture.

SUMMARY

This document relates to methods and materials involved in non-invasively measuring analyte levels in blood and non-invasively detecting abnormal physiological conditions. The presence of marked electrolyte abnormalities (e.g., hyperkalemia, hypokalemia, hypercalcemia, hypocalcemia, magnesium level abnormalities, and glucose levels) and physiological abnormalities (e.g., hypothermia and hypothyroidism) can result in readily apparent and marked derangements on the surface electrocardiogram (ECG) of the patient. These readily apparent and marked derangements can include peaked T wave, progressive QRS widening, the development of a sinusoidal QRS complex, and ultimately arrhythmias.

These ECG changes can reflect the physiologic response of electrical tissues to metabolic derangements and blood level changes. It, however, is useful to assess drug, electrolyte, and analyte levels while they are within the normal range, or only mildly abnormal. These much smaller variations, which can be clinically important, do not generally lead to changes readily identifiable on the surface ECG. As described herein, the application of signal averaging, which can enhance the signal to noise ratio of physiologic signals, in conjunction with algorithmic processing to account for body position changes, respiration, and ectopic complexes can provide sufficient sensitivity to allow assessment of changes in physiologic levels of analytes based on the physiologic response of tissues to those changes. In addition, the use of "band-aid" style ECG patches capable of prolonged recording of electrical signals, respiration, and (via accelerometers) body position can allow for long-term tracking of electrolytes such as potassium. As described herein, signal averaging techniques can be used to detect subtle changes in a surface ECG that are indicative of changes (e.g., physiologic changes) in a blood analytes. Such subtle changes can be undetectable in the absence of a signal averaging technique. The addition of algorithmic processing can lead to determination of analyte levels.

Detecting changes (e.g., physiologic changes) in a blood analytes using the methods and materials provided herein can allow clinicians and other medical personnel to identify patients potentially needing medical intervention (e.g., drug intervention, surgery, or combinations thereof) at a point earlier than would have otherwise been determined or can facilitate outpatient management of conditions such as heart failure, fluid overload, and arrhythmias that might otherwise require hospitalization for frequent blood tests and monitoring.

The methods and materials provided herein can be used to detect analyte changes within a mammal that are smaller than those changes that are visible to the naked eye via an electrical recording. In some cases, the methods and materials provided herein can include performing a baseline "calibrating" blood test. In some cases, the methods and materials provided herein can include algorithmic processing of ECG to compensate for body position, respiration, premature complexes, etc., and can include linear modeling (e.g., multiple linear equations) of ECG segments to account for multiple changes that may occur simultaneously. In some cases, the methods and materials provided herein can include the use of probability modeling (e.g., hidden Markov and maximum likelihood regression) to take into account both ECG changes and clinical variables to produce a final electrolyte value. In some cases, the methods and materials provided herein can include the use of a matrix of ECG changes to account for multiple changes (e.g., the use of the linear equations of FIG. 2 to take into account multiple electrical effects of various electrolytes, and the use of Maximum likelihood linear regression and/or hidden Markov modeling to be applied to the equations generated to diagnose a condition such as a change in potassium levels). In some case, the models described herein can incorporate clinical data such that multiple inputs (e.g., algorithmically adjusted signal averaged ECG, specific ECG changes, and clinical data) can be used to statistically and accurately predict which electrolyte(s) is/are changing and by how much.

In some cases, based on one or more baseline measurements or no blood tests, the methods and materials provided herein can be used to obtain serial electrolyte values over time non-invasively and without the need for additional phlebotomy or with infrequent "calibrating" blood tests. In some cases, the methods and materials provided herein (e.g., a system provided herein) can include the ability to generate alerts to the patient or caregiver when critically abnormal electrolyte values are detected.

In general, one aspect of this document features a method for assessing the level of an analyte within a human. The method comprises, or consists essentially of, obtaining electrocardiogram results from the human and comparing the results to a signal template to obtain an indication of the level of the analyte in the human, wherein the signal template or the electrocardiogram results were generated using a signal averaging technique. The signal template and the electrocardiogram results can be generated using a signal averaging technique. The signal template can represent a level of analyte that is within the normal human physiologic range of levels for the analyte. The signal template can represent a level of analyte that is outside the normal human physiologic range of levels for the analyte. The electrocardiogram results, when compared to the signal template, can indicate that the level of the analyte in the human is within the normal human physiologic range of levels for the analyte. The electrocardiogram results, when compared to the signal template, can indicate that the level of the analyte in the human is outside the normal human physiologic range of levels for the analyte.

In another aspect, this document features a method for assessing a change in the level of an analyte within a human as compared to a previously determined level of the analyte. The method comprises, or consists essentially of, (a) obtaining electrocardiogram results from the human, (b) comparing the results to a signal template to obtain an indication of the level of the analyte in the human, and (c) comparing the level of the analyte in the human to the previously determined level of the analyte to determine the change, wherein the change is a change that is not detectable based on visual inspection of an ECG tracing. The change can be less then 25 percent of the normal physiologic range of the analyte. The change can be less then 20 percent of the normal physiologic range of the analyte. The change can be less then 15 percent of the normal physiologic range of the analyte. The change can be less then 10 percent of the normal physiologic range of the analyte. The change can be less then 5 percent of the normal physiologic range of the analyte.

In another aspect, this document features a method for assessing a change in the level of an analyte within a human as compared to a previously determined level of the analyte. The method comprises, or consists essentially of, (a) obtaining an electrical recording result from an organ within the human, (b) comparing the result to a signal template to obtain an indication of the level of the analyte in the human, and (c) comparing the level of the analyte in the human to the previously determined level of the analyte to determine the change, wherein the change is a change that is not detectable based on visual inspection of an electrical recording of the organ. The organ can be a heart. The electrical recording result can be an ECG tracing.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2 depicts representative ECG data and exemplary equations for determining analyte levels from ECG data, in accordance with some embodiments.

Like reference symbols in the various drawings indicate like elements.

DETAILED DESCRIPTION

Figure 1:
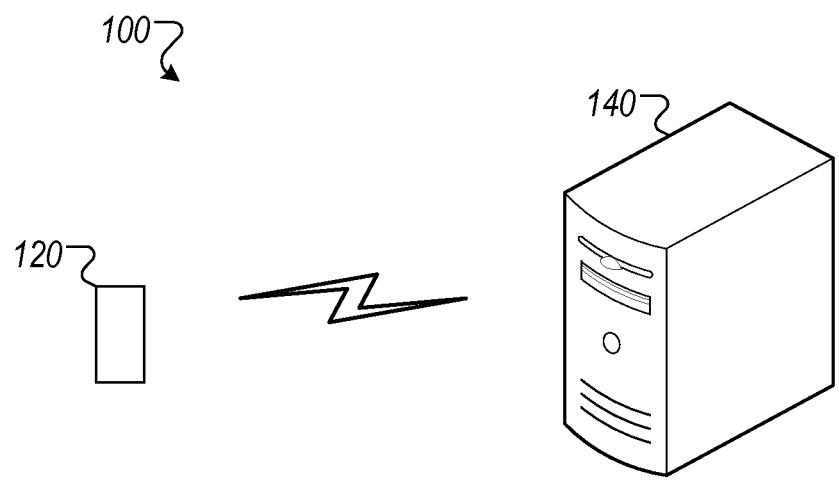
FIG. 1 depicts a schematic representation of a system for the non-invasive monitoring of physiological conditions, in accordance with some embodiments.

Referring to FIG. 1, in some embodiments, a system 100 for the non-invasive detection of physiological conditions includes one or more sensors 120 in communication with a computational device 140. The sensors 120 can be worn on the skin of an individual (e.g., a human) and can non-invasively measure physiological signals (e.g., ECG signals) associated with the individual. While most embodiments described herein relate to the use of passive recording of cardiac electrical signals to assess analytes, it is to be understood that an active system that delivers or injects microAmp to milliamp level currents can be used in addition to or in place of passive recordings to assess, for example, skeletal muscle response (e.g., twitch). Data indicative of the measured signals can be communicated from the sensors 120 to the computational device 140, which can interpret the data and, based at least in part on the data, determine one or more physiological conditions. The transmission of data from sensors 120 to computational device 140 can be performed wirelessly, and system 140 can be a remote server based system. For example, the system 100 can determine the level of one or more analytes in the individual's blood, physiological changes in blood analyte levels, physiologically abnormal levels of blood analytes, physiological abnormalities such as hypothermia, and the like. In some cases, sensors 120 can be ECG patches that permit continuous surface electrocardiographic monitoring. Sensors 120 can be physically embodied in one patch like device or can have a multiplicity of surface electrodes, or be implanted electrodes that communicate wireless with a receiver. Sensors 120 can each include an accelerometer allowing sensor 120 to determine the body position of the wearer, noise elimination algorithms (e.g., to reduce or eliminate the noise associated with skeletal muscle signals, respiration, mechanical motion, and the like), and algorithms for QRS peak detection. In some cases, system 100 can utilize data obtained by sensors 120 to identify changes in an individual's ECG that are not readily apparent to the naked eye. For example, system 100 can identify microvolt changes in wave amplitudes, millisecond changes in wave durations, and the like. Signal averaging of the ECG, with algorithmic binning related to heart rate, body position, respiration, and ectopy (premature complexes) can permit this high sensitivity to minute changes by correcting for these variables. These changes can be further used to, for example, identify changes in blood analyte levels (e.g., within and outside physiologically normal ranges) or identify physiological abnormalities. In one example, sample data from sensors 120 can be compared to previously obtained templates to obtain one or more differences. These differences can be used to determine changes in the level of one or more analytes and identify physiological conditions such as hypothermia.

For example, as depicted in FIGS. 4-6 of the McHenry Martin and Furnas reference ("Identifying Drug-Induced Changes in Electrocardiogram Results of Elderly Individuals," *The Consultant Pharmacist*, 1997), the presence of marked electrolyte abnormalities in the blood (e.g., hyperkalemia, hypokalemia, hypercalcemia, hypocalcemia, high or low magnesium levels, high or low blood glucose levels, and the like), hypothermia, hypothyroidism (e.g. U waves being present on ECG), and the like can be associated with identifiable derangements in a surface ECG. These derangements can include peaked T waves, progressive QRS widening, the development of sinusoidal QRS complexes, arrhythmias, and the like. FIGS. 4-6 of the McHenry Martin and Furnas reference depict some physiologic states that are associated with ECG changes that are visible to the naked eye. For example, FIG. 4 depicts ECG tracings associated with hyperkalemia. In another example, FIG. 5 depicts ECG tracings associated with hypokalemia. FIG. 6 of the McHenry Martin and Furnas reference depicts ECG tracings associated with hypercalcemia and hypocalcemia.

While exaggerated abnormalities in a surface ECG (such as those depicted in the McHenry Martin and Furnas reference or other references such as Wrenn et al., *Ann. Emerg. Med.*, 20:1229-1232 (1991); Aslam et al., *Nephrol. Dial. Transplant.*, 17:1639-1642 (2002); Surawicz, *Am. J. Cardiol.*, 12:656-662 (1963); Surawicz, *Postgrad. Med.*, 55(6):123-9 (1974); VanderArk et al., *Cardiovasc. Clin.*, 5(3):269-94 (1973); and Surawicz, *Am. Heart J.*, 73(6):814-34 (1967)) associated with marked electrolyte or drug abnormalities are identifiable on the surface electrocardiogram using the naked eye, the methods and materials provided herein can be used to identify subtle changes in a surface ECG that are not identifiable on the surface electrocardiogram using the naked eye. Such subtle changes may emerge from physiologic changes in a blood analyte levels (e.g., potassium levels fluctuating within the normal range of about 3.5 to 5.2 mmol/L). While changes in the surface ECG may occur due to the physiologic response of electrically active tissues to these changes in analytes, they may be too subtle to be detected by an individual examining the ECG tracing, and other factors (such as body positions, changes in association with complex prematurity, heart rate, etc.) may mask them. In some cases, the magnitude of change in the ECG due to a change in a physiological condition is small enough when compared to background ECG noise, which can be in the range of 8-10 microVolts (e.g., from skeletal muscles, and the like), that an individual examining the ECG tracing may not be able to distinguish the subtle changes from a normal ECG tracing obtained prior to the change in analyte level. Thus, techniques to enhance the signal to noise ratio and to correct for the other factors (body position, etc.) can be used to retrieve medically useful information from these signals.

In some embodiments, system 100 can detect subclinical and/or clinical changes in a surface ECG that may not be distinguishable with the naked eye by applying signal averaging techniques to the surface ECG data. For example, while a patient is in the same position for a period of time (e.g., greater than one minute, five minutes, ten minutes, and the like), ECG data can be recorded, and the individual cardiac cycles averaged together by system 100 to yield a tracing of a single cardiac cycle that represents an average of the cardiac cycles recorded during the period of time. In one example, a linear, shift-invariant digital filter can be implemented in the time domain as a difference equation or convolution sum. Signal averaging techniques that can be applied include, without limitation, those described elsewhere (see, e.g., Cain et al., *JACC*, 27:238-49 (1996)). In another example, spectral analysis can be used (e.g., by implementing fast Fourier Transforms). In still other examples, averaging can be performed by spatial techniques or temporal techniques.

In some embodiments, system 100 can be configured to acquire reliable, usable surface ECG readings in spite of various phenomenon such as changes in heart rate or changes in position. System 100 can be configured to account for the need for a reliable fiducial point in the tracing to permit averaging, changes in association with ectopy/prematurity, and the like. An example of this is discussed in greater detail below in connection with FIGS. 2 and 3. In some embodiments, sensors 120 include an ECG band-aid "patch" that can perform one or more averaging techniques. Averaging techniques, such as those performed by an ECG band-aid patch can reduce noise to less than 1 microvolt. As such, system 100 can identify microvolt changes in, for example, T-wave amplitude, QRS amplitude, and the like. Furthermore, system 100 can identify changes in, for example, T-wave duration, QRS duration, other ECG morphometric changes, and the like. In one example, averaging techniques can produce a tracing of a cardiac cycle that is an average of multiple cardiac cycles sampled over a period of time. By this process, noise (which is random) is averaged out, leaving the desired signal for analysis. System 100 can compare the averaged cardiac cycle to one or more template cycles (associated with known analyte levels either due to a baseline calibrating blood test or with the use of standard templates) to identify differences between the current signal averaged tracing and the baseline tracing, and thus calculate the change in analyte level.

While system 100 can identify large differences in wave amplitude (e.g., greater than 10 microvolts) and in wave durations (e.g., greater than 50 milliseconds), techniques such as averaging and spectral analysis can allow system 100 to identify small differences in wave amplitude (e.g., less than 10 microvolts) and in wave durations (e.g., less than 50 milliseconds). In some embodiments, system 100 can incorporate the identified differences into algorithms that can account for absolute changes in cardiac waveforms (e.g., a 10 microvolt decrease in T-wave amplitude, a 50 millisecond increase in QRS complex duration, and the like) and relative changes (e.g., a 20% increase in QRS complex amplitude, a 10% decrease in T-wave duration, and the like). The algorithms included in system 100 can be used to determine, for example, blood analyte levels (by determine the change from a baseline tracing with associated known analyte level or by matching the present tracing to a standardized template), changes in physiologic electrolytes, changes in medication levels in the blood, and/or physiologic abnormalities that affect the activity of electrically active tissue.

Figure 3:
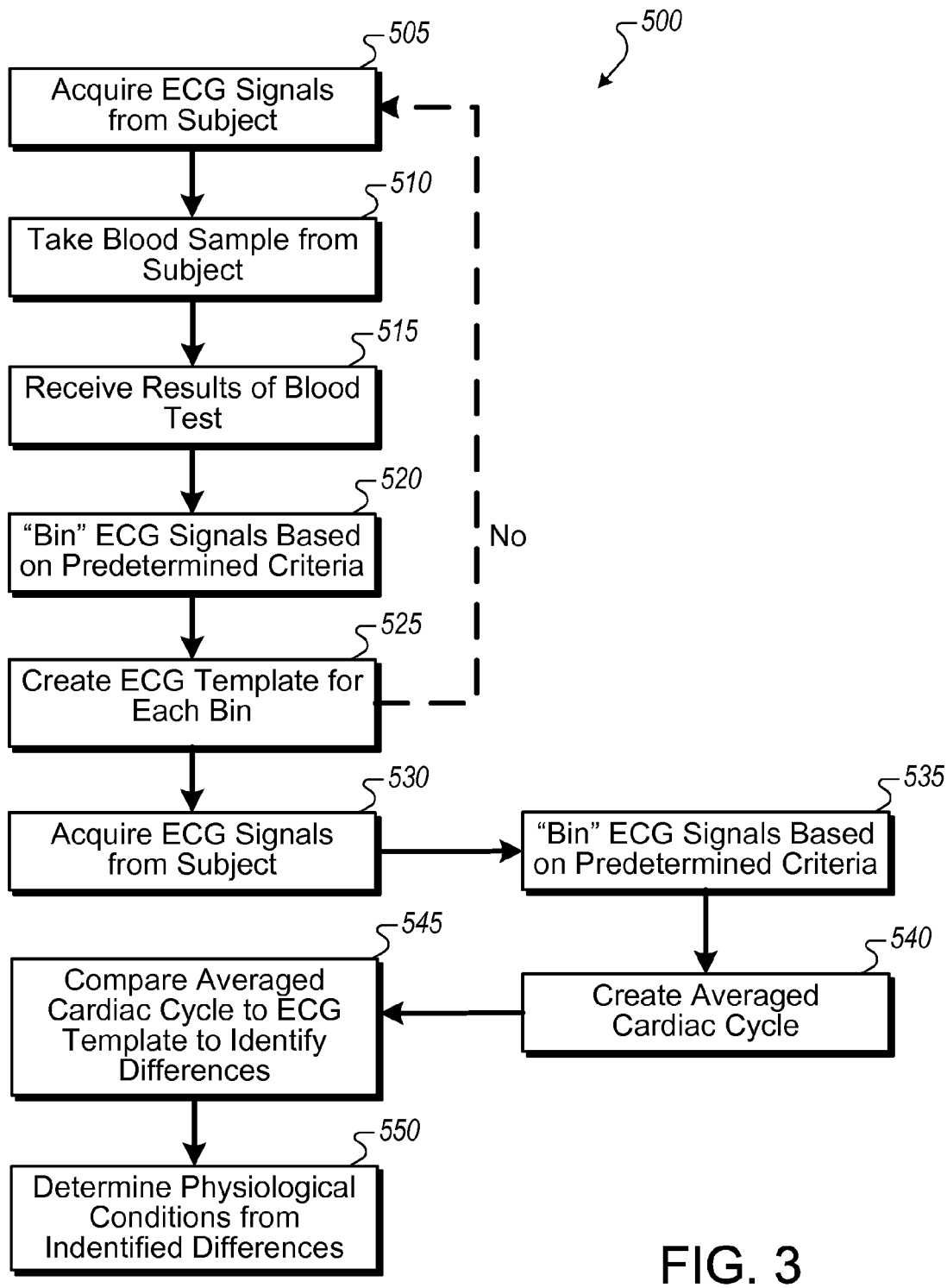
FIG. 3 depicts a process (e.g., an algorithmic process) for determining analyte levels from ECG data, in accordance with some embodiments.

Referring in more detail to the illustrative process 500 shown in FIG. 3, process 500 for detecting physiological conditions of a subject can be performed by system 100. For example, system 100 can non-invasively measure and/or determine changes in analyte levels of the subject (e.g., levels of calcium, potassium, magnesium, glucose, and the like), determine levels and monitor the effects of pharmaceuticals (e.g., digoxin, Class I-C anti-arrhythmia drugs, sotalol, dofetilide, amiodarone, beta blockers, calcium channel blockers, tricyclic antidepressants, lithium, and the like), and detect physiological abnormalities (e.g., acute myocardial infarction, subarachnoid bleed, fluid accumulation around the heart, and the like). In some embodiments, system 100 can monitor for compliance with avoidance of drugs such as cocaine, amphetamines, marijuana, and the like.

In operation 505, system 100 can acquire ECG signals from a subject that can be used later to create one or more baseline templates. The ECG signals can be acquired from the subject while in different body positions (e.g., supine, prone, on side, sitting up, or standing) and with varying heart rates. For example, the subject could remain sedentary with a substantially resting heart rate and spend a period of time (e.g., more than 1 minute, 5 minutes, and the like) in each of several body positions. The subject could then perform some exercise to elevate his heart rate and repeat the body positions. With use of a patch electrode system, no specific action may be required on the subjects part as the patch can determine body position using accelerometers or other MEMs devices, and acquire and bin data for each given position while the subject happens to be in that position for later analysis.

In operation 510, a blood sample can be taken from the subject at substantially the same time as the ECG signals were acquired during operation 505, thus yielding a correlation between the blood sample and the ECG signals. In operation 515, results of one or more baseline blood tests performed on the sample taken in operation 510 can be entered into system 100. For example, the blood level of potassium, as determined by a blood test, can be entered into system 100. While potassium is discussed in this example, it is recognized that any number of results representing physiologic electrolytes (e.g., calcium, magnesium, glucose, and the like), pharmacologic agents (e.g., digoxin, Class I-C anti-arrhythmia drugs, sotalol, dofetilide, amiodarone, beta blockers, calcium channel blockers, tricyclic antidepressants, lithium, and the like), other drugs (e.g., cocaine, amphetamines, marijuana, and the like) can be entered into system 100. While in this example, a "calibration" blood sample is used, it is recognized that it is possible that use of pre-formed templates can eliminate the need for calibration blood. In some cases, for some analytes, more than one sample of blood to calibrate the system at two or more calibration levels can be used to increase accuracy.

In operation 520, system 100 can categorize, or "bin," each of the individual cardiac cycles obtained during operation 505 based on predetermined criteria such as heart rate range, body position, and the like. In some embodiments, individual cardiac cycles can be examined for abnormalities, the presence of which can cause system 100 to discard the abnormal cardiac cycle. For example, cardiac cycles including complexes exceeding a predefined prematurity index can be excluded to eliminate potential changes in the surface ECG due to ectopy. In some cases, respiration can be measured using impedance measurements or other known methods and used to further refine the signal (e.g., binning all end expiration or end inspiration signals). In operation 525, the contents of each bin can be used to create an ECG template (e.g., a cardiac cycle that is an average of all the cardiac cycles contained in the bin) that is indicative of a body position and range of heart rates for the potassium level determined from the blood sample in operation 505. Optionally, operations 505 through 525 can be repeated at different times to acquire data for different blood analytes and or different blood analyte levels.

At desired intervals (e.g., hourly, daily, twice daily, every 20 minutes, and the like), system 100 can execute operation 530 causing system 100 to obtain surface ECG measurements for a period of time (e.g., greater than one minute, greater than five minutes, five to ten minutes, ten minutes, and the like). In operation 535, system 100 can bin the individual cardiac cycles from the ECG measurement based on body position and heart rate. In operation 540, the resulting bins can be averaged creating one or more averaged cardiac cycles, one for each of the bins from operation 535. The resulting averaged cardiac cycles can be compared in operation 545 to corresponding templates to determine differences between the averaged and template cardiac cycles. For example, an averaged cardiac cycle created from cardiac cycles obtained when the subject was supine with a heart rate between 60 and 70 beats per minute can be compared to a template created during operation 525 for the supine position with a heart rate between 60 and 70 beats per minute. In operation 550, the resulting differences, such as differences in wave amplitude, duration, and morphologies, can be included in one or more algorithms to determine physiological conditions such as blood analyte levels, physiological abnormalities, and the like. For example, the differences can be included in a calculation to determine the concentration of potassium in the subject's blood. In this way, the physiologic effects of one or more electrolytes, which are known, can be recorded on the ECG and used to calculate the blood value present to result in the ECG obtained.

In some embodiments, such as described herein in connection with process 500, templates can be created for different heart rate ranges to correct for changes in cardiac cycles based on heart rate. In other embodiments, adjustments can be made to the differences found between an averaged cardiac cycle and a template cycle based on differences in the heart rate of the subject during sampling as opposed to during the template formation. In yet other embodiments, specific algorithms for determining analyte levels, and the like, can include adjustment factors that take into account different heart rates. Similarly, adjustments can be made based on the body position of the subject.

In some embodiments, system 100 can be used in a variety of situations including patients with renal dysfunction, patients who are undergoing medication changes, patients on diuretic therapy, patients with heart failure, and the like. In some cases, this may facilitate hospital dismissal with regular assessment of blood analytes without the need for active phlebotomy. In other cases, patients can be monitored while at home, without the need for collecting blood samples. In some embodiments, algorithms used to determine physiological conditions (such as levels of blood analytes) can correct for changes resulting from medications taken by the subject so as not to skew the results.

In some embodiments, the surface ECG obtained from a body-worn patch can be signal averaged to provide a very high signal to noise ratio, thus providing accuracy down to the microvolt level. This can permit the detection of minute changes in the electrocardiogram obtained from a subject. For example, system 100 can be used to detect minute ECG changes that are the result of changes in blood analyte levels that are within the physiologic range to detect abnormalities and trends before blood levels become dangerous and the ECG changes become overtly visible. Detecting these minute changes can be used to identify changes within the physiologic range of values for electrolytes such as potassium, magnesium, calcium, glucose, and the like. In some embodiments, the levels of antiarrhythmic drugs including amiodarone, propafenone, flecainide, and the like can be evaluated. For example, ambulatory "bloodless blood tests" can be performed by system 100 since changes in the ECG that are too small to be seen by the naked eye could be detected with signal averaging techniques. This can permit determination of blood levels of analytes based on their physiologic effects on the ECG. In some circumstances, the use of remote monitoring ECG band-aids, such as those described herein, could provide ambulatory values of various analytes. Determination of blood analyte levels can be performed at different times, thus showing potential trends. In a similar manner, system 100 can be used to identify clinical conditions, such as subarachnoid hemorrhage, stroke, cardiac ischemia, and the like.

In some embodiments, stepwise, temporal changes in ECG tracings (or signal averaged ECGs) can be used to identify a disease or a change in condition. For example, system 100 can be used to identify a sequence of changes that occur in a stepwise fashion versus known or set templates (e.g., first or serial blood test measurement(s) with set ECG template). For example, system 100 can be used to establish a set of ECG templates for a subject for a known status (e.g., one or more analyte levels based on blood tests, a known amount of medication/agent given in a controlled setting, and the like), over a given range (e.g. glucose levels at various amounts), and over a given period of time (e.g., at the time of a single bolus of agent followed over a course of time with corresponding ECG changes at given time points). In analyzing ECG changes, the timing of insulin administration, consuming a meal, and the like can influence the significance of the ECG changes. A change detected in the subject's ECG can have more weight if it occurs at one time relative to another time. For example, a change in a diabetic's ECG two hours after receiving insulin and/or consuming a meal can be more important than a change detected 5 minutes after the insulin/meal.

In some embodiments, system 100 can be used to monitor compliance to medication dosages and intervals in patients and to customize dosages for a patient. For example, the identification of a known ECG change can indicate that a medication was taken correctly. Furthermore, system 100 can alert a monitoring service that a medication has just been taken (e.g., based on the identification of a known change in the ECG that is indicative of the medication having been taken). In addition, dosages can be personalized to an individual based on identified ECG changes. Thus, dosages can be adjusted until a preferred change in the patient's ECG is identified. This is particularly desirable with a number of medications (e.g., flecainide, sotalol, and others) for which absence of ECG changes indicate subtherapeutic dosing, and excessive ECG changes indicate potential toxicity. In some embodiments, system 100 can be used to alert an individual that a medication (e.g., insulin) should or should not be taken, that a meal should be consumed, that some action should be performed to treat a condition, and the like. In some embodiments, system 100 can be used to determine an individual's capacity to metabolize a drug based on ECG changes identified over time after the drug has been taken. In some embodiments, other parameters (e.g., heart rate, blood pressure, and the like) can be used by system 100 when performing the functions described herein. Furthermore, the functions described herein can be performed by system 100 utilizing other forms of ECG monitoring. For example, system 100 can utilize skin based surface monitors, implantable monitors (e.g. pacemakers, defibrillators, and the like, including all recording electrodes and pathways that these device incorporate), subcutaneous monitors, and the like. In some embodiments, system 100 can assess analytes in patients with implanted cardiac devices based on threshold assessment to a high level of precision (e.g., millivolt levels or microvolt levels). It is known that changes in electrolytes change capture thresholds in pacing systems. This change in capture thresholds can be used to calculate analytes levels (e.g., physiological electrolytes, medications, and the like). In some cases, additional processing can be used to better identify the intervals required for analysis. For example, the voltage derivative over time (dV/dt) can be used to identify the T wave peak as a surrogate for QT duration to assess analyte and drug changes, or any number of transforms can be used (Fourier, Hilbert, etc.) to make these determinations.

Referring to FIG. 2, algorithms used by system 100 to determine physiologic conditions of a subject (e.g., analyte levels, physiologic abnormalities, and the like) can incorporate values determined by analyzing the ECG data of the subject, comparing ECG data to predetermined ECG templates, and the like. For example, an algorithm provided herein can take into account absolute values, numerical changes in values relative to a template, percentage changes in values relative to a template, and ratios of said values associated with, for example, the amplitude of P waves, PR intervals, PR segment elevation or depression, QRS durations, ST segment elevation and shape, T-wave amplitudes, U-wave amplitudes, and the like. An exemplary equation used to determine the change in an electrolyte level is:

$$\Delta E_1 = F_{11} \times PR_A + F_{21} \times P_{AM} + F_{31} \times PR_{elevation} + F_{41} \times QRS \text{ duration} + \ldots \text{ (with terms for each ECG segment)}$$

where each factor F can apply a relative weight to a specific ECG change for the given electrolyte of interest, $PR_A$ is the change in PR segment length, $P_{AM}$ is the amplitude of the P wave, $PR_{elevation}$ is the increase in amplitude of the PR segment, and QRS duration is the length of the QRS complex. Additional terms can be added to account for values of, changes in, and ratios of other ECG segments. In one example of potassium analysis (as is described in greater detail below), the largest initial factors F would be those associated with the T wave whereas ECG elements that do not contribute to potassium analysis would have an F coefficient value of 0. By this means, the mathematics of matrix algebra can be applied to analyze multiple analyte changes simultaneously, and temporal changes made can allow for system "learning."

In some embodiments, system 100 includes an analysis of specific states, with the sequence of progression from one state to another providing additional algorithmic weight. For example, in hyperkalemia, specific states in sequential order may develop as potassium levels progressively increase. Thus, there may initially be peaking of the T wave. A next step may be widening of the QRS complex. A subsequent change may include relative diminution or nonrecognition of P waves and ultimately of a sinusoidal pattern. Later states could include morphologic changes (such as notching) beyond those described above, or the development of arrhythmias. System 100 can recognize this progression of states and apply additional algorithmic weight to equations associated with potassium levels and changes.

In some embodiments, system 100 can assess multiple electrolyte changes simultaneously, with corrections/adjustments as needed for potential overlapping effects on some segments of the ECG based on other electrolyte changes. In some embodiments, when a specific change is identified by system 100 (e.g., increased T wave amplitude), an algorithmic scan of all potential causes of T wave peaking can be performed to exclude other causes. For example, if T waves peak, ST segments can be analyzed to exclude ischemia as the cause, while PR and QRS intervals can be assessed to determine which changes are likely due to potassium changes. Maximum likelihood linear regression and/or hidden Markov modeling can be applied to the equations generated to diagnose the condition (e.g., changes in potassium levels), and the equation itself would define the change in potassium from a known baseline value. In some embodiments, this modeling would not be restricted to ECG data, but can also incorporate clinical information. For example, in a patient with diabetes on insulin, changes in the QT interval would preferentially be attributed to glucose changes, and in a patient on flecainide, changes in the QRS duration would be preferentially attributed to drug effect. Additionally, other information extracted from the ECG (e.g., heart rate variability [HRV], analysis of cycle length in the time and frequency domains, and the like) can be integrated in the predictive models. For example, hypoglycemia can cause both Q-Tc (corrected QT interval) prolongation and HRV changes consistent with increased autonomic tone.

The methods and material provided herein can be used to measure or detect passive recording of physiologic signals for analysis. As described herein, in some cases, an ECG patch can be configured to deliver a small electrical stimulus and to capture skeletal muscle responses. For example, an analysis of the magnitude of mechanical twitch, and of conduction time from the stimulating electrode to a nearby recording electrode can provide additional information as to the physiological status of electrically active tissue (in this case skeletal muscle), and can be used alone or algorithmically in combination with other measurements recorded as described herein to determine analyte levels. In some cases, maximal handgrip strength can be assessed to follow changes in calcium and or potassium, and skeletal muscle stimulation can be used in combination with accelerometer measurements to detect jerky movements, quivering of muscles, etc.).

Examples of Specific Analytes and Serial ECG Changes

Referring again to FIGS. 4-6 of the McHenry Martin and Furnas reference, physiological changes in a subject (e.g., changes in analyte levels outside of physiologic range, physiological abnormalities, and the like) can cause changes in the subject's ECG tracing that can be clearly visible to the naked eye. However, fluctuations in the subject's ECG, such as those described below, may first occur in magnitudes small enough such that they are not clearly discernible as definitive changes to the naked eye, but can be identified by system 100 when signal averaging techniques are applied. Thus, system 100 can identify physiological conditions before their effects are readily apparent on the subject's ECG tracing. For many of the physiological conditions and analytes described below (e.g., potassium, calcium, pharmaceuticals, and the like), the effects on the averaged ECG measurements can reach several millivolts or more, however, early detection can be made by system 100 while the effects are still on the order of 1-5 microvolts. Similarly, changes in the segment interval measurements can range from 50-100 msec (e.g., in the case of marked electrolyte changes), however, early detection is possible using system 100 while these changes are on the order 5 msec. Changes in cycle length with drug administration could be up to the 100 msec range.

Normal reference ranges for various analytes (e.g., potassium, glucose, calcium, and magnesium) are described elsewhere (University of Kentucky' Clinical Lab Reference Range Guide dated Mar. 14, 2006 (see, e.g., internet cite: "www" dot "hosp" dot "uky" dot "edu" slash "ClinLab" slash "report" dot "pdf"). For calcium, the normal reference range can be between 8.8 and 10.0 mg/dL. For glucose (fasting), the normal reference range can be between 80 and 99 mg/dL. For magnesium, the normal reference range can be between 1.8 and 2.4 mg/dL. For potassium, the normal reference range can be between 3.6 and 4.9 mmol/L.

Potassium

ECG changes are most likely attributed to fluctuations in potassium levels in patients with renal dysfunction, or who are on medications that are known to affect potassium levels, such as diuretics, ACE inhibitors, and angiotensin receptor blockers. In some embodiments, system 100 can take into account these factors when using probability modeling, such as described previously, and can give additional weight to potassium level fluctuations as the source of ECG changes.

For example, elevations in serum potassium levels can result in increased T-wave amplitude, increased PR interval duration, increased QRS duration, and diminished P-wave amplitude. In cases of extreme changes in serum potassium levels (such as shown in FIGS. 4-6 of the McHenry Martin and Furnas reference), bradycardia, sinus arrest, ventricular tachycardia, and ventricular fibrillation may occur. In another example, decreasing levels of serum potassium can result in diminished T-wave amplitude, ST segment depression, increased Q-T interval, development of U waves and an increase in U wave amplitude. In cases of extreme hypokalemia, ventricular tachyarrhythmias may ensue.

Magnesium

Increases in serum magnesium levels can result in electrocardiographic changes such as, increased PR segment duration, increased QRS duration, increased T wave, and increased cycle length. Decreases in magnesium levels can have opposite effects (e.g., decreased PR segment duration, decreased QRS duration, decreased T wave, decreased cycle length, and the like).

Calcium

Increasing calcium levels can result in shortening of the Q-Tc interval, while decreasing calcium levels can result in Q-Tc interval prolongation.

Glucose

Glucose measurements can be critically important due to their role in managing diabetes mellitus. This can require frequent access to blood to titrate glucose lowering therapies in accordance with meals and physical activity. Thus, the ability to non-invasively measure ambulatory glucose levels can have a major impact on the management of this important condition.

There have been numerous studies assessing the affects of glucose blood levels with regards to arrhythmogenesis and with cardiac cellular physiology. Many human and animal studies which have been performed using either insulin clamps or other modes of controlling glucose levels have had difficulty differentiating the role of glucose itself on the surface ECG versus concomitant changes that occur in potassium and adrenaline associated with changes in glucose (most notably, extreme levels of hypo or hyperglycemia.) However, this complexity may not be an issue in that clinically, changes in glucose can cause consistent changes in these other variables leading to ECG changes. Thus, system 100, which can be capable of assessing multiple electrolyte changes simultaneously, can extrapolate glucose level changes from one or more averaged electrocardiograms.

Exemplary changes that can be useful for screening for increasing levels of glucose from baseline can include Q-Tc interval shortening, increasing T wave amplitude, decreasing QRS amplitude:T-wave amplitude ratio, changing T-wave shape, and shortening R-R interval (e.g., a shortening over time indicates a steady rise in glucose concentration). Exemplary changes that can be useful for screening for decreasing levels of glucose from baseline can include Q-Tc interval prolongation, diminution of the T wave, depression of the ST segment depression, and shortening R-R interval (e.g., the rate of change can be rapid and the magnitude of change can be large, in contrast to the shortening over time as seen in increasing glucose concentrations).

In some cases, this technique can be used as an alarm of high and/or low blood sugar to warn diabetics to take action when they become insensitive to detecting changes in their own physiology.

Digoxin

As digoxin levels increase, electrocardiographic changes can be identified, such as decreasing heart rates (increase in cycle length), increasing PR interval, shortening of the Q-T interval, and depression of the ST segment depression with a specific curved upwards curvature/morphology.

Acute Myocardial Infarction.

Acute myocardial infarction can be indicated by electrocardiographic changes such as giant pointed T waves, ST segment elevation (curved upwards), and the development of Q waves.

Subarachnoid Bleed

In elderly patients who are frail, screening for subarachnoid bleed can be clinically useful. The following ECG changes can suggest screening in an otherwise independent living person to see whether there have been neurologic changes to suggest subarachnoid hemorrhage. Thus, a sensor 120 (e.g., a band-aid patch) worn on an independent living person and monitored by the system 100 can raise an alert to suggest that an individual may need help. Exemplary ECG changes associated with subarachnoid hemorrhage can include an increase in P-wave and T-wave amplitude, shortening of the PR interval, prolongation of the Q-T interval, and the development of tall U waves.

Class I-C Antiarrhythmic Drugs

There are stereotypical changes that are predicted with introduction of medication such as flecainide and propafenone. For example, the QRS duration can increase. An increase in the QRS duration of less than 10% may suggest sub-therapeutic drug levels. An increase above 20% (e.g., above 25%) can increase the risk of toxicity. In other examples, the PR interval can prolong and the cycle length can prolong (heart rate slows).

In patients who have a genetic variation in the metabolism of propafenone, there may be a more significant heart rate slowing relative to the other physiologic changes due to accumulation of metabolites with increased beta blocker effect. Thus, in increase in cycle length in excess of other parameter changes may identify slow metablizers. Other exemplary ECG changes seen with increasing levels of propafenone may include the development of first degree, second degree, or third degree AV block or the development of bundle branch block. In patients receiving propafenone and flecainide, the abrupt development of bundle branch block could suggest drug toxicity. Additionally, at normal heart rates (under 100 beats per minute), the development of a right bundle branch block pattern with a downward sloping segment could indicate the presence of a late Brugada syndrome. This is a very rare genetic disease that can be unmasked by drug administration. Average PR interval prolongation and QRS duration can be closely correlated with dosage increases and concomitant levels in plasma concentrations of drugs. Therefore, these specific ECG changes can be detected by the system 100 and can be used for monitoring for administration and compliance, and excluding toxicity.

Sotalol and Dofetilide

Administration of sotalol or dofetilide can result in increasing Q-Tc interval prolongation. With administration of sotalol, a Q-Tc interval increase of less than 10% can indicate that the dosage may be subtherapeutic; where as an increase in 20% or more may be associated with toxicity. In another example, if the Q-T interval is greater than 500 msec, or in the setting of a bundle branch block if the Q-Tc is greater than 550 msec or the JT interval is greater than 440 msec, then toxicity is possible and decreasing the drug dose may be indicated. With dofetilide, a resting Q-Tc interval of greater than 440 msec can be a contraindication (greater than 500 msec bundle branch block if present). Following the first dose, if the Q-Tc increase is greater than 15%, or is greater than 500 msec (550 msec in the setting of bundle branch block), the dose can be decreased. If during follow up the Q-Tc interval exceeds 500 msec (550 msec in the setting of a bundle branch block) the medication nay be discontinued. Due to the availability of prolonged ambulatory monitoring by the system 100, the risk of drug toxicity may be significantly decreased by detecting Q-Tc interval prolongation over time. Since Q-Tc interval can be affected by drug clearance which may be a function of renal function, patients who undergo situations such as dehydration or fluctuations in renal function can have their risk of toxicity diminished by prolonged ambulatory monitoring.

Amiodarone

Administration of amiodarone can result in similar electrophysiologic changes in the Q-T interval (prolongation), as well as cycle length and PR interval lengthening.

Beta Blockers and Calcium Channel Blockers

These drugs can cause prolongation of R-R intervals, prolongation of the PR segment, and heart block.

As described herein, system 100 can be used to manage medication (e.g., compliance, dosage, metabolism, toxicity, personalization over time and over course of disease/therapy, and the like). Additional medications that can be monitored include tricyclic antidepressants and lithium. In some embodiments, toxins (e.g., produced by the body, from foreign organisms, and the like) can be detected at low levels by system 100, prior to becoming serious conditions. In some embodiments, system 100 can be used to monitor and follow conditions such as pericardial effusion and pericarditis (fluid around the heart). For example, ECG changes due to fluid accumulation around the heart can include a smaller ECG, a smaller QRS complex, beat-to-beat alternations in QRS amplitude, and the like. In some embodiments, system 100 can be used to assess EMG and/or mechanical motion of muscle in response to a stimulus to measure analyte levels. The threshold to elicit muscle contraction could also determine changes in analytes (e.g., calcium, potassium, and the like).

In some embodiments, system 100 can be used to monitor compliance with avoidance of narcotics (e.g., patch monitoring of illegal drugs). For example, the presence of cocaine, amphetamines, and/or marijuana can be identified by the presence of tachyacardias on the ECG. System 100 can be used to monitor a patient during the administration of QT prolonging drugs (e.g., albuterol, alfuzosin, amantadine, amiodarone, amitriptyline, amphetamines, astemizole, atazanavir, atomoxetine, chloroquine, clomipramine, dolasetron, metaproterenol, moxifloxacin, phentermine, and the like).

A number of embodiments of the invention have been described. Nevertheless, it will be understood that various modifications may be made without departing from the spirit and scope of the invention. Accordingly, other embodiments are within the scope of the following claims.

What is claimed is:

1. A method for assessing the level of an analyte within a human, the method comprising:
   (a) generating, using a signal averaging technique, electrocardiogram results from said human; and
   (b) comparing said results to a signal template to obtain an indication of the level of said analyte in said human,
   wherein said analyte is potassium, magnesium, calcium, or glucose.

2. The method of claim 1, further comprising generating, using the signal averaging technique, said signal template.

3. The method of claim 1, wherein said signal template represents a level of analyte that is within the normal human physiologic range of levels for said analyte.

4. The method of claim 1, wherein said signal template represents a level of analyte that is outside the normal human physiologic range of levels for said analyte.

5. The method of claim 1, wherein said electrocardiogram results, when compared to said signal template, indicate that the level of said analyte in said human is within said normal human physiologic range of levels for said analyte.

6. The method of claim 1, wherein said electrocardiogram results, when compared to said signal template, indicate that the level of said analyte in said human is outside said normal human physiologic range of levels for said analyte.

7. The method of claim 1, wherein said analyte is potassium.

8. The method of claim 1, wherein said analyte is magnesium.

9. The method of claim 1, wherein said analyte is calcium.

10. The method of claim 1, wherein said analyte is glucose.

11. A method for assessing a change in the level of an analyte within a human as compared to a previously determined level of said analyte, wherein said method comprises:

(a) generating, using a signal averaging technique, electrocardiogram results from said human,
(b) comparing said results to a signal template to obtain an indication of the level of said analyte in said human, and
(c) comparing the level of said analyte in said human to said previously determined level of said analyte to determine a change,
wherein said change is a change that is not detectable based on visual inspection of an ECG tracing, and
wherein said analyte is potassium, magnesium, calcium, or glucose.

12. The method of claim 11, wherein said change is less than 25 percent of the normal physiologic range of said analyte.

13. The method of claim 11, wherein said change is less than 20 percent of the normal physiologic range of said analyte.

14. The method of claim 11, wherein said change is less than 15 percent of the normal physiologic range of said analyte.

15. The method of claim 11, wherein said change is less than 10 percent of the normal physiologic range of said analyte.

16. The method of claim 11, wherein said change is less than 5 percent of the normal physiologic range of said analyte.

17. The method of claim 11, wherein said analyte is potassium.

18. The method of claim 11, wherein said analyte is magnesium.

19. The method of claim 11, wherein said analyte is calcium.

20. The method of claim 11, wherein said analyte is glucose.

21. A method for assessing a change in the level of an analyte within a human as compared to a previously determined level of said analyte, wherein said method comprises:
(a) generating, using a signal averaging technique, an electrical recording result from an organ within said human,
(b) comparing said result to a signal template to obtain an indication of the level of said analyte in said human, and
(c) comparing the level of said analyte in said human to said previously determined level of said analyte to determine a change,
wherein said change is a change that is not detectable based on visual inspection of an electrical recording of said organ, and
wherein said analyte is potassium, magnesium, calcium, or glucose.

22. The method of claim 21, wherein said organ is a heart.

23. The method of claim 21, wherein said electrical recording result is an ECG tracing.

24. The method of claim 21, wherein said analyte is potassium.

25. The method of claim 21, wherein said analyte is magnesium.

26. The method of claim 21, wherein said analyte is calcium.

27. The method of claim 21, wherein said analyte is glucose.

* * * * *